(12) United States Patent
Meyer

(10) Patent No.: US 7,217,274 B2
(45) Date of Patent: May 15, 2007

(54) INJECTOR WITH FINGER RING

(75) Inventor: Rolf Meyer, Port (CH)

(73) Assignees: Anton Meyer & Co. AG, Nidau (CH); Asico LLC, Westmont, IL (US)

( * ) Notice: Subject to any disclaimer, the term of this patent is extended or adjusted under 35 U.S.C. 154(b) by 646 days.

(21) Appl. No.: 10/338,893

(22) Filed: Jan. 9, 2003

(65) Prior Publication Data
US 2004/0097954 A1    May 20, 2004

(30) Foreign Application Priority Data
Nov. 18, 2002   (EP)   ................................. 02405992

(51) Int. Cl.
*A61F 9/00*   (2006.01)
(52) U.S. Cl. ...................... 606/107; 623/6.12
(58) Field of Classification Search ................ 606/107; 623/6.11, 6.12
See application file for complete search history.

(56) References Cited

U.S. PATENT DOCUMENTS

| 4,145,124 | A | * | 3/1979 | Weisgerber | ................. 351/121 |
| 4,836,202 | A | * | 6/1989 | Krasner | ..................... 606/107 |
| 5,643,276 | A | | 7/1997 | Zaleski | |
| 5,728,102 | A | | 3/1998 | Feingold et al. | |
| 6,179,843 | B1 | | 1/2001 | Weiler | |

* cited by examiner

*Primary Examiner*—Kevin T. Truong
(74) *Attorney, Agent, or Firm*—Browdy and Neimark, PLLC

(57) ABSTRACT

A hand-operated injector for inserting a lens into an eye has a grip body (1) with a lens holder (13) for holding a lens, and a plunger (2) arranged displaceably in the grip body (1) for guided insertion of the lens into the eye. An actuating means (5, 6) for displacing the plunger (2) relative to the grip body (1) is arranged on the plunger (2), which actuating means (5, 6) is rotatable relative to the plunger (2). The injector can thus be rotated through any desired angle, without having to substantially change the position of the hand pressing on the plunger (2), in particular the position of the thumb.

9 Claims, 2 Drawing Sheets

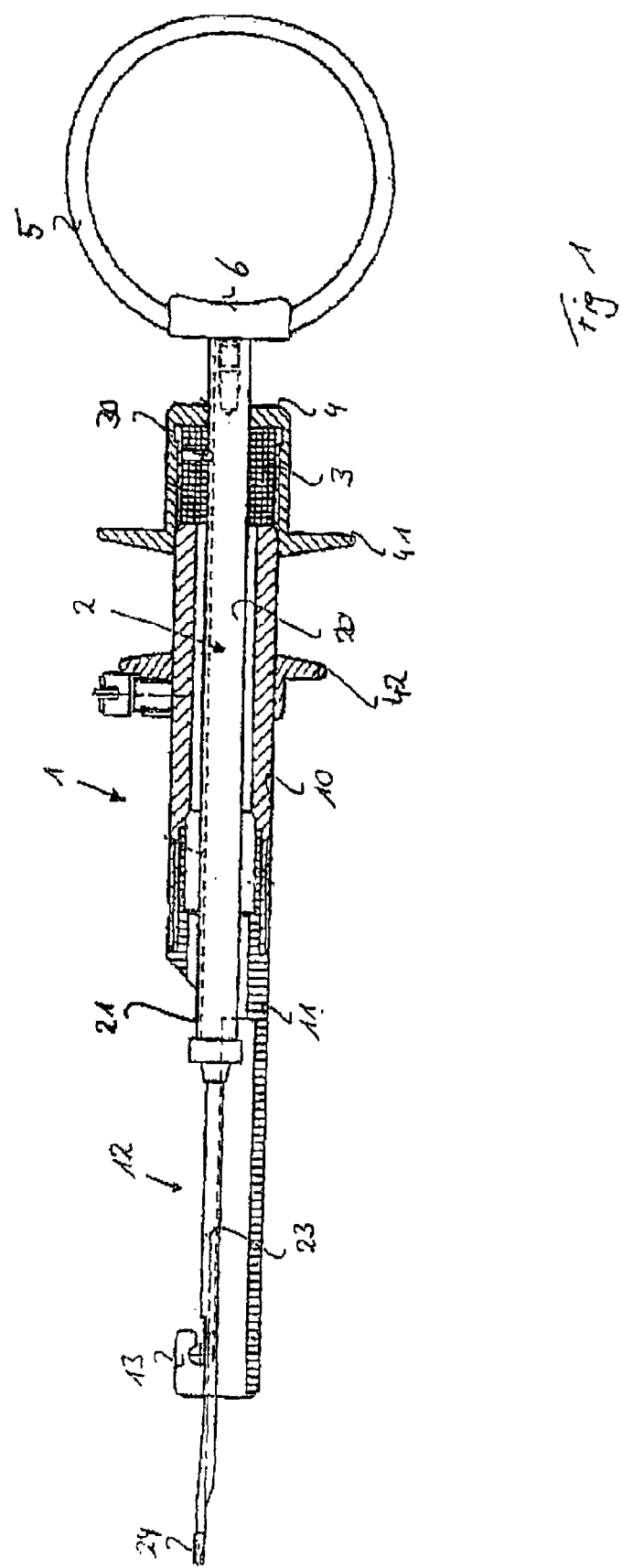

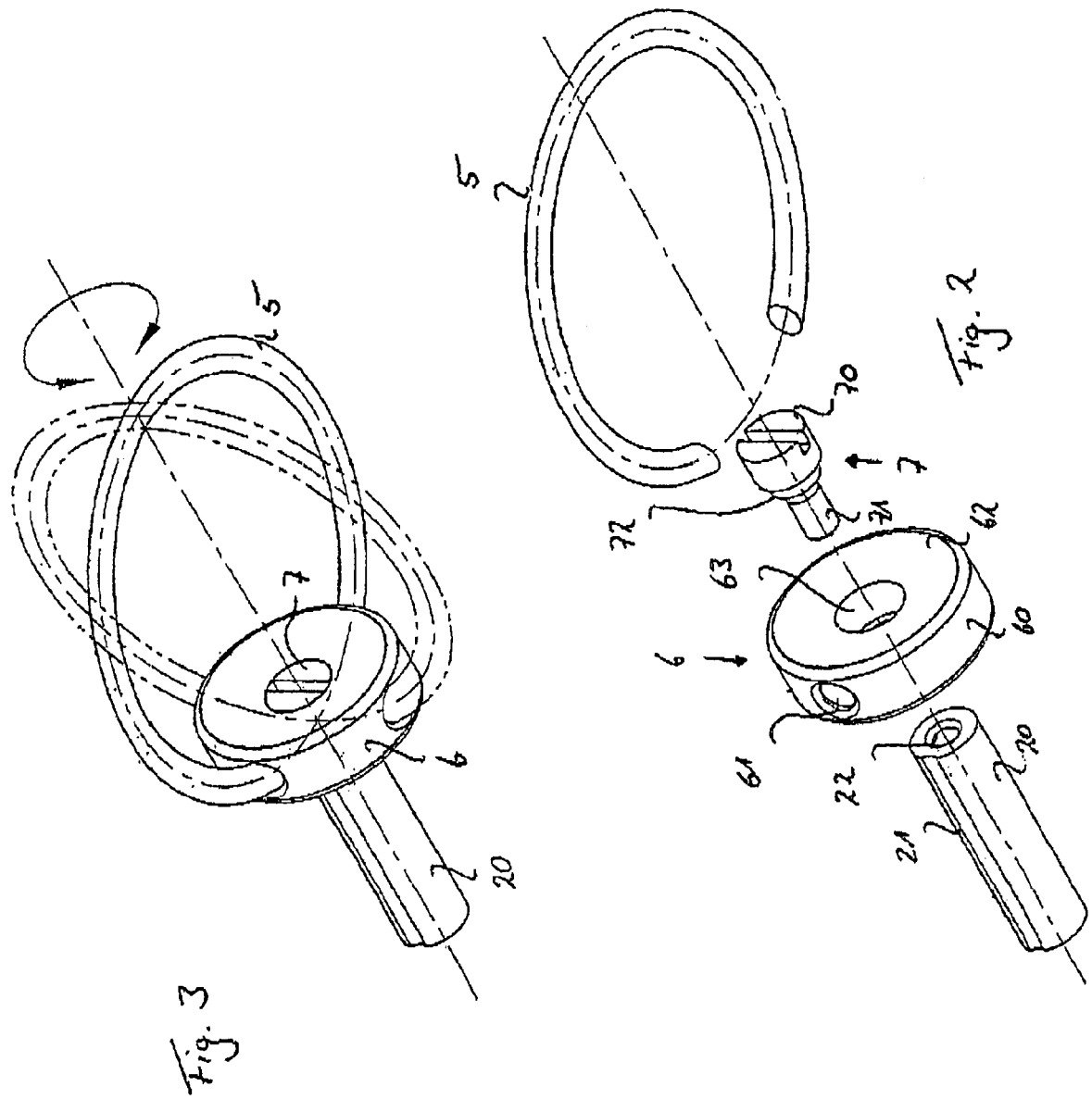

INJECTOR WITH FINGER RING

TECHNICAL FIELD

The invention relates to a hand-operated device for inserting a lens into an eye,

TECHNOLOGICAL BACKGROUND

Nowadays, in ophthalmic surgery, replacing an opaque natural eye lens with an artificial lens is one of a number of routine procedures. However, this procedure requires that the surgeon has a very steady hand and has had a great deal of practice.

For this reason, hand-operated devices referred to as injectors are known which permit a certain degree of guiding when fitting the artificial lens. These known injectors generally have a grip body, and a plunger which can be displaced in the grip body via a thread. In the front area of the grip body there is a lens holder into which an artificial lens to be inserted is placed. By rotating the plunger, this lens can then be pushed through a front opening of the lens holder, the lens being folded in the process, if appropriate. By further advancing the lens, it is introduced in the folded state into the eye. An injector of this kind is disclosed, for example, in U.S. Pat. No. 5,643,276.

Moreover, the applicant's European patent application EP 01 810 823, which is still to be published, describes a hand-operated injector which permits use by one hand but nevertheless guarantees exact guiding of the plunger. In this injector, the plunger is mounted so as to be laterally displaceable in a ball-bearing bush. The precise lateral displacement is ensured by a guide groove into which a guide element arranged in the grip body engages. In one embodiment, the plunger is laterally displaceable but fixed in terms of rotation In another embodiment, the plunger has a spiral in order to permit a rotation of the plunger at the end of the insertion movement. This makes it easier to insert the artificial lens, in particular to unfold it in the eye. However, this rotation is predetermined by the design of the injector, in particular of the spiral.

SUMMARY OF THE INVENTION

It is an object of the invention to make available a device, of the type mentioned in the introductory part, with which the surgeon can determine the time and the extent of the rotational movement himself, without however adversely affecting the exact guidance and stable hold of the device.

This object is achieved by a device having the features of a handheld device for inserting a lens into an eye, said device having a grip body with a lens holder for holding a lens, and a plunger arranged displaceably in the grip body for guided insertion of the lens into the eye, an actuating means for displacing the plunger relative to the grip body being arranged on the plunger, said actuating means being rotatable relative to the plunger and comprising a finger ring.

The device according to the invention has a plunger which is displaceable in a grip body and which has an actuating means. According to the invention, the actuating means is rotatable relative to the plunger.

In this way, it is possible for the surgeon to hold the injector and insert the lens safely into the eye with one hand. If at any time during the operation, particularly when the lens is inserted in the eye, he wishes to rotate the lens, this can be done by rotating the plunger or grip body, without the actuating means also rotating. The hand, or the thumb of this hand, does not have to change position. It is thus possible for the surgeon to rotate the device by hand, preferably with the other hand, without compromising the stable hold of the injector.

In a simple embodiment, the actuating means consists of a plunger head with a suitably shaped end face for actuating the plunger.

In a preferred embodiment, a finger ring, particularly for a thumb, is arranged at the plunger head.

Further advantageous embodiments will become evident from the dependent claims,

BRIEF DESCRIPTION OF THE DRAWINGS

The subject of the invention is explained below with reference to a preferred illustrative embodiment which is depicted in the attached drawings, in which;

FIG. 1 shows a cross section through an injector according to the invention;

FIG. 2 shows an exploded view of part of a plunger with an actuating means according to the invention, and FIG. 3 shows a perspective view of the actuating means according to the invention, with part of the plunger, in two positions of rotation.

PREFERRED EMBODIMENTS OF THE INVENTION

A hand-operated device according to the invention used for inserting a lens into an eye and referred to as an injector is shown in FIG. 1.

It is constructed in substantially the same way as the injector in aforementioned European patent application EP 01 810 823. The content of the latter, and that of the U.S. application Ser. No. 10/224,321 claiming this priority, are included here by reference.

The injector has an injector body or grip body 1 in which a plunger 2 is displaceably mounted. Both grip body 1 and plunger 2 are preferably made of metal, in particular titanium.

The grip body 1 has a sleeve 10 which merges at its front end into a grip front part 11. At its forward end directed away from the sleeve 10, the grip front part 11 has a lens holder 13, a suitable artificial lens being inserted via an insert window 12 which is arranged behind the lens holder 13.

The plunger 2 has a plunger rod 20 which merges into a plunger needle 23 with a plunger tip 24. The plunger needle 23 is preferably connected releasably to the plunger rod 20, so that a new needle can be used depending on the nature of the lens. In addition, it can also be used as a disposable needle, The plunger rod 20 can be made in one piece or in several pieces.

The plunger 2 and its plunger rod 20 are arranged to be displaceable in a guided manner in the sleeve 10. In the example shown here, a ball-bearing bush 3 is provided for this purpose which is fixed in position in the sleeve 10. It is preferably arranged in the rear end of the sleeve 10 remote from the plunger tip 23. The plunger rod 20 preferably has a guide groove 21, and a guide element 30, preferably a resilient metal or plastic ball, is arranged in the sleeve 10, in the ball-bearing bush 3 or in another part fixed to the sleeve 10. The guide element 30 engages in the guide groove 21 and thus permits an improved guidance of the plunger 2 upon its displacement relative to the grip body 1. The guide groove 21 is preferably rectilinear, so that the plunger 2 is laterally, i.e., longitudinally, displaceable but fixed in terms of rotation.

As can be seen in FIG. 1, the grip body 1 is preferably closed off by a closure cap 4 through which the plunger 2 passes. Flanges 41, 42 are preferably arranged on the closure cap 4 and/or on the grip body and, in the same way as in a syringe, they serve as a support for the surgeon's fingers. The second flange 42 is preferably a separate element which can be secured releasably on the sleeve 10 via a securing means, in this case a screw. In this way, the second flange 42 can be displaced along the sleeve 10, so that the distance between the two flanges 41, 42 can be adapted to the thickness of the surgeon's fingers.

Arranged at the rear end of the plunger 2 remote from the plunger tip 24, there is an actuating means for displacing the plunger 2 relative to the grip body 1. According to the invention, this actuating means can be rotated relative to the plunger 2, so that a rotation of the grip body 1 results in a rotation of the plunger 2, but not a rotation of the actuating means. It is preferably rotatable through 360°, although it is also possible to permit only a pivoting movement.

In the example shown here, the actuating means comprises a plunger head 6 and a finger ring 5, in particular a thumb ring. These can be seen best in FIGS. 2 and 3.

The finger ring 5 is arranged fixed in position on the plunger head 6. The plunger head 6 is designed as a flat cylinder with a central through-opening 63. A shoulder is present in the through-opening 63. The plunger head 6 is connected to the rear end of the plunger rod 20 by means of a locking screw 7. The plunger rod 20 for this purpose has a threaded bore 22 in which a screw thread 71 of the locking screw 7 engages. Between screw head 70 and screw thread 71, the locking screw 7 has a shoulder 72 which is slightly longer in the axial direction than that of the plunger head 6. In addition, the screw head 70 is slightly smaller in diameter than the through-opening 63. In this way, the plunger head 6 can be rotated relative to the plunger rod 20 and to the locking screw 7. The free end face 62 of the plunger head 6 or press button serves as a press surface for the finger, in particular the thumb, of the surgeon for pushing the plunger through the injector. The end face 62 can be designed flat or can have a depression to better receive the thumb.

Two insertion openings 61 are present in the generated surface 60 of the plunger head 6. These insertion openings 61 are preferably arranged diametrically opposite one another. The open finger ring 5 can be inserted into these insertion openings, as can be seen in FIG. 2. This arrangement has the advantage that the finger ring 5 can be selected according to the thickness of the surgeon's fingers and can be easily mounted on the injector.

In addition, the actuating means described above has the advantage that it consists of relatively few parts which can be easily fitted and dismantled, so that the actuating means can be optimally cleaned.

The actuating means can also have another shape or can consist of other elements as long as it allows the surgeon to move the plunger 2 forward and in so doing to hold the injector steadily in its predetermined position.

The rotatable actuating means according to the invention can also be used in other hand-operated injectors. In this connection, all injectors which can be operated with one hand are preferred.

The device according to the invention thus permits a rotation of the injector through any desired angle, without having to substantially change the position of the hand pressing on the plunger, in particular the position of the thumb.

LIST OF REFERENCE NUMBERS 1 grip body
10 sleeve
11 grip front part
12 insert window
13 lens holder
2 plunger
20 plunger rod
21 guide groove
22 threaded bore
23 plunger needle
24 plunger tip
3 ball-bearing bush
30 guide element
4 closure cap
41 first flange
42 second flange
5 finger ring
6 plunger head
60 generated surface
61 insertion opening
62 end face
63 through-opening
7 locking screw
70 screw head
71 screw thread
72 shoulder

The invention claimed is:

1. A hand-operated device for inserting a lens into an eye, said device comprising:
 a grip body with a lens holder for holding a lens,
 a plunger arranged displaceably in the grip body for guided insertion of the lens into the eye, the plunger comprising a plunger rod, and a plunger needle connected to a first end of the plunger rod, and
 an actuating means for displacing the plunger relative to the grip body being arranged on the plunger, said actuating means being rotatable relative to the plunger so that a rotation of the grip body results in a rotation of the plunger but not a rotation of the actuating means, said actuating means comprising
 a split finger ring having two non-touching ends, and
 a plunger head rotatably secured on the second end of the plunger rod, said plunger head comprising a flat cylinder and two openings defined in a circumferential surface of the plunger head diametrically opposite to one another, the two ends of the finger ring being configured so as to be inserted into the two openings.

2. The device as claimed in claim 1, wherein the finger ring can be secured fixed in position on the plunger head.

3. The device as claimed in claim 1, wherein the finger ring has a diameter of such a size that it can receive a surgeon's thumb.

4. The device as claimed in claim 1, wherein the plunger can be displaced longitudinally relative to the grip body but fixed in terms of rotation.

5. The device as claimed in claim 1, wherein the plunger has a guide groove, and wherein at least one guide element is arranged in the grip body and engages in the guide groove.

6. The device as claimed in claim 1, wherein the plunger is displaceable in a guided manner in a ball-bearing bush which is arranged in a rotationally fixed manner in the grip body.

7. The device as claimed in claim 1, further comprising a bush connected to the grip body so as to be rotationally fixed therein.

8. The device as claimed in claim 1, wherein the plunger rod comprises a threaded bore defined within a second end of the plunger rod, and the device further comprises a locking screw configured to be inserted into the threaded bore of the plunger rod through the central through-opening of the plunger head, to rotatably connect the plunger head to the plunger rod.

9. A hand-operated device for inserting a lens into an eye, said device comprising:
- a grip body with a lens holder for holding a lens,
- a plunger arranged displaceably in the grip body for guided insertion of the lens into the eye, the plunger comprising a plunger rod, and a plunger needle connected to a first end of the plunger rod, the plunger rod comprising a threaded bore defined within a second end of the plunger rod, and
- an actuating means for displacing the plunger relative to the grip body being arranged on the plunger, said actuating means being rotatable relative to the plunger so that a rotation of the grip body results in a rotation of the plunger but not a rotation of the actuating means, said actuating means comprising
- a plunger head rotatably secured on the second end of the plunger rod, said plunger head comprising a flat cylinder having a central through-opening defined in a center portion thereof, and
- a finger ring secured to said plunger head, and
- a locking screw configured to be inserted into the threaded bore of the plunger rod through the central through-opening of the plunger head, to rotatably connect the plunger head to the plunger rod.

* * * * *